United States Patent [19]

Hall

[11] Patent Number: 4,458,071
[45] Date of Patent: Jul. 3, 1984

[54] PROCESS FOR 1-OXA-β-LACTAMS

[75] Inventor: David A. Hall, Indianapolis, Ind.

[73] Assignee: Eli Lilly and Company, Indianapolis, Ind.

[21] Appl. No.: 442,080

[22] Filed: Nov. 16, 1982

[51] Int. Cl.³ .......................................... C07D 498/04
[52] U.S. Cl. ..................................................... 544/90
[58] Field of Search ........................................ 544/90

[56] References Cited
U.S. PATENT DOCUMENTS 4,150,156 4/1979 Beattie et al. ................. 544/90
4,366,316 12/1982 Yoshioka et al. .............. 544/90

Primary Examiner—Richard Raymond
Attorney, Agent, or Firm—William B. Scanlon; Arthur R. Whale

[57] ABSTRACT

An azetidin-2-one-4-sulfinic acid represented by the formula

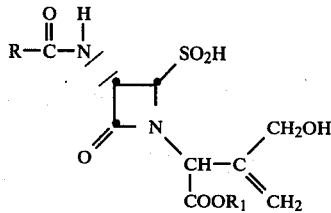

is reacted with Pb(OAc)$_4$ in liquid SO$_2$ containing CuII ion to provide isomeric cyclization products of the formulas

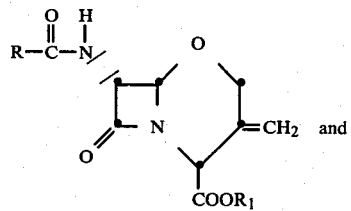 and

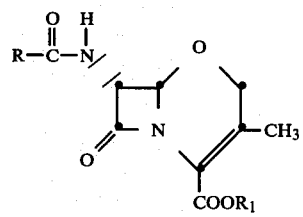

wherein R is e.g. benzyl, phenoxymethyl, benzyloxy, diphenylmethoxy, and R$_1$ is a carboxy-protecting group. The products of the process are useful intermediates for 1-oxa-β-lactam antibacterials.

9 Claims, No Drawings

PROCESS FOR 1-OXA-β-LACTAMS

BACKGROUND OF THE INVENTION

This invention relates to a process for preparing 1-oxa-β-lactam antibiotic compounds. The 1-oxa-β-lactam compounds, also referred to as 1-oxa (dethia) cephalosporin compounds, have been described by Narisada et al., U.S. Pat. No. 4,138,486, Christensen et al., U.S. Pat. No. 4,226,866, and Wolfe, U.S. Pat. No. 4,013,653. The 1-oxa-β-lactam compounds represent a new class of antibiotics possessing interesting antibacterial properties. Current methods employed for the synthesis of these compounds involve multi-steps which are often low-yielding and difficult to control with respect to the desired stereochemistry. Because of these difficulties in the synthesis of the 1-oxa-β-lactam compounds, new and simpler synthetic processes are sought.

SUMMARY OF THE INVENTION

This invention relates to a process for the preparation of 1-oxa-β-lactam compounds which comprises the cyclization of a 1-(2-hydroxymethyl-3-protected carboxy-prop-1-ene-3-yl)-3-epi-acylaminoazetidin-2-one-4-sulfinic acid with lead tetraacetate. Following the cyclization, the product is isolated and can be purified by chromatography in the esterified form. After purification the carboxy-protecting group is removed to provide the active form of the 1-oxa-β-lactam compound.

DETAILED DESCRIPTION

According to the process of this invention, a 3α-acylamidoazetidin-2-one-4-sulfinic acid is cyclized with lead tetraacetate preferably in the presence of a carbonium ion stabilizing compound to a mixture of 7α-acylamido-3-exomethylene-1-oxa-β-lactam-4-carboxylic acid ester and the corresponding 3-methyl-1-oxa-β-lactam ester as shown in the following reaction scheme.

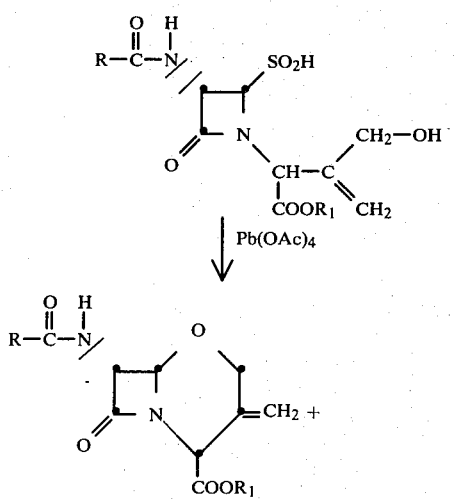

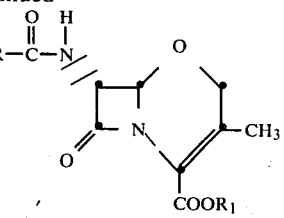

where in the above formulas R is hydrogen, $C_1$–$C_4$ alkyl, $OCH(CH_3)_2$, $HOOC(CH_2)_3$, or an α-(protected amino)-4-carboxybutyl group represented by the formula

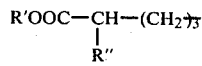

wherein R' is a carboxy-protecting group and
R'' is a protected amino group; or R is a group represented by the formula

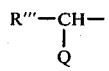

wherein R''' is thienyl, furyl, tetrazolyl, 1,4-cyclohexadienyl, cyclohexenyl, phenyl, or a substituted phenyl group represented by the formula

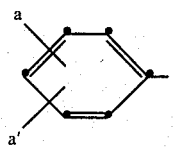

wherein a and a' independently are hydrogen, $C_1$–$C_4$ alkyl, fluoro, chloro, protected amino, protected aminomethyl, protected carboxy, protected carboxymethyl, carbamoyl, $C_1$–$C_4$ alkoxy, or protected hydroxy; Q is hydrogen, protected amino, protected carboxy, or protected hydroxy; or R is an aryloxymethyl group represented by the formula

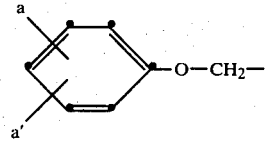

wherein a and a' have the same meanings as defined above; or R is an alkoxy or substituted alkoxy group represented by the formula

wherein R'''' is $C_1$–$C_5$ alkyl, $C_3$–$C_6$ cycloalkyl, benzyl, benzyl substituted by $C_1$–$C_4$ alkyl, $C_1$–$C_4$ alkoxy, or chlorine; diphenylmethyl or diphenylmethyl substituted by $C_1$–$C_4$ alkyl, $C_1$–$C_4$ alkoxy, or chlorine; and $R_1$ is a carboxy-protecting group.

The process is carried out in an inert organic solvent at a temperature between about −25° C. and about 0° C. with lead tetraacetate in an amount corresponding to between about 1.0 mole and about 2.5 moles per mole of the azetidin-2-one-4-sulfinic acid.

The process is preferably carried out in the presence of a dipolar aprotic compound, such as sulfur dioxide or sulfolane, which appears to affect a stabilizing influence on an intermediate carbonium ion of the azetidin-2-one. The preferred compound for this use is liquid sulfur dioxide. Generally, an excess of the dipolar aprotic compound is employed, for example a 2-3 molar excess. The dipolar aprotic compound can serve as the solvent in the reaction or can be used along with an inert organic solvent.

Inert organic solvents which can be used are aprotic solvents such as ester, e.g. methyl acetate, ethyl acetate, isopropyl acetate, methyl propionate and like esters; halogenated hydrocarbon solvents such as methylene chloride, dichloroethane, trichloroethane, and the like; ethers such as tetrahydrofuran; and dioxane and like solvents.

The addition of a source of copper II ion has a beneficial effect on the yield of the reaction, and it is believed the cupric ion assists in the generation and stabilization of the intermediate carbonium ion of the azetidinone. Copper sulfate is a readily available source of copper II ion and generally about 1 g to about 1.5 g of the copper II salt for between 1 and about 2 moles of the azetidin-2-one sulfinic acid is sufficient.

The process, which results in cyclization of the starting material to the 1-oxa-β-lactam compound, proceeds rapidly. For example, on a small scale of about 1 mole the process is essentially complete in about 10-15 minutes. In carrying out a preferred embodiment of the process, the azetidin-2-one-4-sulfinic acid is dissolved in liquid sulfur dioxide and lead tetraacetate and copper sulfate are added to the solution with stirring. The reaction mixture is stirred in the cold for between about 20 and about 30 minutes. The course of the reaction can be followed by chromatography, preferably analytical HPLC. When the reaction is complete, a water immiscible organic solvent such as ethyl acetate is added to the reaction mixture and the whole is washed with a 1:1 mixture of brine and pH 7 phosphate buffer. The organic layer is separated and is washed further with the pH 7 phosphate buffer-brine mixture. After drying, the organic layer is evaporated to dryness to provide the cyclized reaction product, the 1-oxo-β-lactam compound described above. The product is purified by chromatography, preferably HPLC on reversed phase $C_{18}$ silica gel chromatography.

The process of this invention affords a reaction product mixture comprising the isomeric 3-exomethylene-1-oxa-β-lactam ester and the corresponding isomer, 3-methyl-Δ3-1-oxa-β-lactam compound, as described by the structural formulas hereinabove. These isomeric cyclization products can be separated by preparative thin-layer chromatography on silica gel, by column chromatography over silica gel, and by preparative HPLC by employing reversed phase $C_{18}$ silica gel. Alternatively, if the 3-methyl isomer is the desired product, the reaction product mixture comprising the two isomers can be treated with an organic base such as triethylamine or pyridine to effect the isomerization of the 3-exo isomer to the endo 3-methyl isomer. The latter is then recovered and purified by chromatography.

In carrying out the process of this invention with a starting material represented by the formula I wherein R is an alkoxy or substituted alkoxy group, R''''O, lead tetraacetate effects the cyclization without the need of a carbonium ion stabilizing reagent such as for example sulfur dioxide or copper II ion as described above. In this embodiment of the present invention, the compound of the formula I wherein R is an alkoxy or substituted alkoxy group is reacted in an anhydrous aprotic solvent with tetraacetate and the cyclized product is recovered as described hereinabove. When, however, R in formula 1 represents a group other than an alkoxy or substituted alkoxy group, the cyclization reaction is best carried out as described hereinabove with a carbonium ion stabilizing reagent such as sulfur dioxide and with copper II ion.

In carrying out the process of this invention, any free amino, carboxy, or hydroxy groups present in the starting material represented by the formula 1 are protected or blocked to prevent their interference in the process. However, the hydroxy group of the 2-hydroxymethyl-3-protected carboxy-propene-3-yl radical attached to the azetidinone is unprotected, as shown by the structure of formula 1. Amino-protecting groups which can be employed in the process include those amino-protecting groups commonly employed in the β-lactam antibiotic art, for example in the cephalosporin art, and which are stable under the conditions of the process. Illustrative of such amino-protecting groups are the alkoxycarbonyl and substituted alkoxycarbonyl groups such as t-butyloxycarbonyl, methoxycarbonyl, ethoxycarbonyl, cyclopentyloxycarbonyl, adamantyloxycarbonyl, cyclohexyloxycarbonyl, benzyloxycarbonyl, and like groups; the acyl groups forming amides such as acetyl and substituted acetyl, for example chloroacetyl, dichloroacetyl, trifluoroacetyl, and like acyl groups; the benzyl and substituted benzyl groups such as methoxybenzyl and methylbenzyl, diphenylmethyl groups, and like amino-protecting groups.

Carboxy-protecting groups which can be employed to block or protect free carboxylic acid functions during the process of this invention are the carboxy-protecting groups commonly employed in the β-lactam art, for example in the penicillin and cephalosporin arts. Examples of such carboxy-protecting groups include, for example, the alkyl and substituted alkyl groups such as t-butyl, and t-amyl, the benzyl and substituted benzyl groups such as 4-methoxybenzyl, 3,5-dimethoxybenzyl, methylbenzyl, e.g., 4-methylbenzyl, diphenylmethyl, 4-methoxydiphenylmethyl, 4,4'-dimethoxydiphenylmethyl, and like groups; 1-oxysuccinimido, 1-oxyphthalimido, and like carboxy-protecting groups.

Any free hydroxy groups, be they attached to an aliphatic carbon or an aromatic carbon (phenols), may be protected by commonly employed hydroxy-protecting groups, for example with acetyl and substituted acetyl groups, for example chloroacetyl, trifluoroacetyl, and the like; or they can be protected with tetrahydropyranyl, or like hydroxy-protecting groups. Other amino, carboxy, and hydroxy-protecting groups which can be employed in the process of this invention are illustrated in chapters 2, 3, 4, and 5 of *Protective Groups in Organic Chemistry*, Ed. J. F. W. McOmie, Plenum Press, New York, 1973.

The protective groups employed in the process of this invention are used solely for the temporary protection of the amino, carboxy, or hydroxy groups. The methods for their synthesis and removal from the protected group are well known in the art. Generally, these groups are removed by hydrolytic procedures or by hydrogenolysis over a hydrogenation catalyst such as palladium on carbon or Raney nickel.

With respect to the starting materials represented by the formula 1, illustrative acyl groups attached to the amino group in the 3-position of the azetidin-2-one ring are formyl, acetyl, propionyl, butyryl, isobutyryl, and like straight and branched chain acyl groups.

When R in the formula 1 is an α-(protected amino)-4-carboxybutyl group, the acyl moiety is the protected α-amino adipoyl group which is the side chain of cephalosporin C. This acyl radical is represented by the following formula

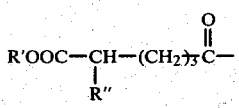

wherein R' is a carboxy-protecting group as defined hereinabove and R" is a protected amino group. In addition to the readily removable amino-protecting groups defined hereinabove, R" is a substituted amino group substituted by acetyl, chloroacetyl, propionyl, benzoyl, halobenzoyl such as 2-chlorobenzoyl, 4-chlorobenzoyl, 2,4-dichlorobenzoyl, 3,4-dichlorobenzoyl, 3-chlorobenzoyl, 2-carboxy-3,4,5,6-tetrachlorobenzoyl, phthaloyl, phenylacetyl, or phenoxyacetyl. These latter amino-protecting groups are preferred protecting groups for the α-aminoadipoyl group as described hereinafter.

Examples of acyl groups R—C(O)— when R is an arylmethyl group represented by the formula

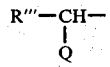

are 2-thienylacetyl, 3-thienylacetyl, 2-furylacetyl, tetrazolylacetyl, 1,4-cyclohexadien-1-ylacetyl, cyclohex-1-ene-1-ylacetyl, cyclohex-2-ene-1-ylacetyl, phenylacetyl, 4-chlorophenylacetyl, 2-methoxyphenylacetyl, 2,6-dimethoxyphenylacetyl, 3-methylphenylacetyl, 2,4-dimethylphenylacetyl, 4-t-butylphenylacetyl, 4-fluorophenylacetyl, 3-(t-butyloxycarbonyl)phenylacetyl, 4-(diphenylmethoxycarbonyl)phenylacetyl, 4-carbamoylphenylacetyl, 2-(benzyloxycarbonylaminomethyl)phenylacetyl, 4-(benzyloxycarbonylmethyl)phenylacetyl, 3-(t-butyloxycarbamido)phenylacetyl, 2-phenyl-2-(t-butyloxycarbamido)acetyl, 2-phenyl-2-(benzyloxycarbamido)acetyl, 2-phenyl-2-formyloxyacetyl, 2-phenyl-2-(diphenylmethoxycarbonyl)acetyl, 2-(2-thienyl)-2-(diphenylmethoxycarbonyl)acetyl, 2-(4-tetrahydropyranyloxyphenyl)-2-(4-methoxybenzyloxycarbonyl)acetyl, 2-(2-furyl)-2-benzyloxycarbamido)acetyl, 2-(cyclohex-1,4-diene-1-yl)-2-(cyclopentyloxycarbamido)acetyl, and like acyl groups.

Examples of acyl groups RC(O)— of the formula 1 when R is aryloxymethyl group as defined above are phenoxyacetyl, 4-methylphenoxyacetyl, 4-fluorophenoxyacetyl, 4-chlorophenoxyacetyl, 3,4-dimethoxyphenoxyacetyl, 3-(benzyloxycarbamido)phenoxyacetyl, 4-(t-butyloxycarbonyl)phenoxyacetyl, 4-carbamoylphenoxyacetyl, 2-(t-butyloxycarbamidomethyl)phenoxyacetyl, and like acyl groups.

Illustrative examples of acyl groups RC(O)— of the formula 1 when R is an alkoxy or substituted alkoxy group represented by the formula

are methoxycarbonyl, ethoxycarbonyl, isoamyloxycarbonyl, t-amyloxycarbonyl, t-butyloxycarbonyl, cyclopropyloxycarbonyl, cyclobutyloxycarbonyl, cyclopentyloxycarbonyl, cyclohexyloxycarbonyl, benzyloxycarbonyl, 4-methylbenzyloxycarbonyl, 4-chlorobenzyloxycarbonyl, 3,4-dimethoxybenzyloxycarbonyl, diphenylmethoxycarbonyl, 4-methoxydiphenylmethoxycarbonyl, 4,4'-dimethyldiphenylmethoxycarbonyl, and like acyl groups which form urethanes with the 3-amino group of the azetidine-2-one.

A preferred embodiment of the process of this invention comprises the use of a starting material represented by the formula 1 wherein R is an alkoxy group or a substituted alkoxy group. Especially preferred starting materials in the process of this invention are represented by the formula 1 wherein R is benzyloxy or a substituted benzyloxy group. Examples of the starting materials are 1-(2-hydroxymethyl-3-diphenylmethoxycarbonylprop-1-ene-3-yl)-3α-benzyloxycarbamidoazetidin-2-one represented by the formula

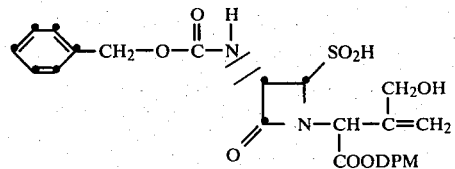

wherein DPM is diphenylmethyl, and the corresponding benzyl ester represented by the formula

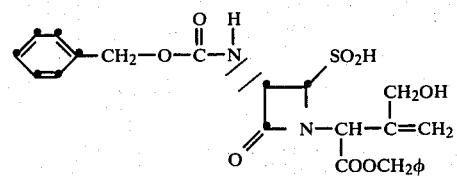

According to this preferred embodiment, the 3α-benzyloxycarbamidoazetidin-2-one-4-sulfinic acid diphenylmethyl ester represented by the above formula is dissolved in sulfur dioxide and a small amount of copper sulfate is added. Thereafter, at least one molar equivalent of lead tetraacetate is added and the reaction mixture is stirred for approximately 15 minutes while the temperature is maintained between about −10° C. and about 0° C. and the product is recovered as described hereinabove by extraction with ethyl acetate. The mixture of the 3-exomethylene product and its isomer, the 3-methyl 1-oxa-β-lactam compound, are separated by chromatography over silica gel, preferably by high performance liquid chromatography employing $C_{18}$ reverse phase silica gel.

In another preferred embodiment of this invention, a preferred starting material in the form of its diphenylmethyl ester is dissolved in ethyl acetate and between 1 and about 2 molar equivalents of lead tetraacetate is added to the solution with stirring while the temperature is maintained between about −15° C. and 0° C. The reaction is agitated by vigorous stirring for approximately 30 minutes. The product is recovered by first filtering the insolubles, washing the filtrate containing the products with a mixture of brine and pH 7 phosphate buffer, and then drying and evaporating the washed solution to dryness. The crude mixture of products is then purified by chromatography.

As described hereinabove in the description of the process of this invention, both the 3-exomethylene and the 3-methyl isomer thereof are obtained in the process. It appears that the 3-exomethylene 1-oxa-β-lactam compound is obtained and is at least partially isomerized to the 3-methyl isomer either during the process or during the workup of the reaction product mixture. The 3-exomethylene isomer upon treatment with an organic base such as a tertiary alkylamine, for example triethylamine or a cyclic amine such as pyridine, quinoline, or isoquinoline, isomerizes to the 3-methyl isomer.

The starting materials employed in the process of this invention represented by the formula 1 are prepared as described in co-pending application Ser. No. 442,075 filed Nov. 16, 1982. As described therein, the azetidin-2-one-4-sulfinic acids represented by the formula 1 are prepared by the electrolysis of a 7α-acylamino-3-hydroxymethyl-3-cephem-4-carboxylic acid ester 1,1-dioxide. According to the process, a 3-hydroxymethyl cephalosporin ester 1,1-dioxide represented by the formula

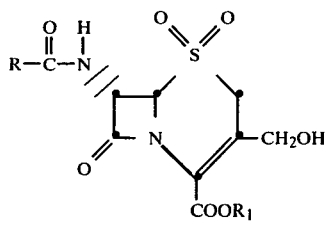

wherein R and $R_1$ have the same meanings as described above for the formula 1, is reduced at the cathode of an electrolysis cell comprising a mercury pool cathode, a platinum anode, and a cationic resin separating the cathode and anode compartments. A suitable electrolyte can be sodium perchlorate, lithium perchlorate, or sodium acetate. The anolyte is preferably phosphate buffer pH 2.7.

The reduction is carried out preferably at a temperature between about −10° C. and about 10° C. and at a reduction potential between about 1.0 v. and about −1.9 v. vs. a standard calomel electrode.

The 3-hydroxymethyl sulfone ester is dissolved in methyl alcohol containing a proton source such as an organic acid, e.g. acetic acid. The electrolyte of choice, e.g. sodium acetate, is then added to the solution to achieve a 0.1M concentration of the electrolyte.

The solution is then placed in the cathode compartment and the electrolysis apparatus is flushed with argon until any oxygen present is removed. The electrolysis can be carried out at constant potential or at constant current. The progress of the electrolysis can be followed by use of analytical HPLC on an aliquot of the reduction mixture.

Following the electrolysis the reduction product mixture is extracted in the cold with a water immiscible organic solvent, preferably ethyl acetate.

The 7α-acylamino-3-hydroxymethylcephalosporin 1,1-dioxides employed in the electrolysis providing the azetidin-2-one-4-sulfinic acids are obtained with 7β-acylaminocephalosporanic acids. The cephalosporanic acid is first oxidized to the corresponding sulfone and the 7β-acylamino side chain of the sulfone is epimerized to the 7α-acylamino epimeric sulfone. The epimeric sulfone acid is then deacylated at the 3′-position to provide the 7α-acylamino-3-hydroxymethyl-3-cephem-4-carboxylic acid 1,1-dioxide.

The above sequence of reactions is illustrated by the following reaction scheme.

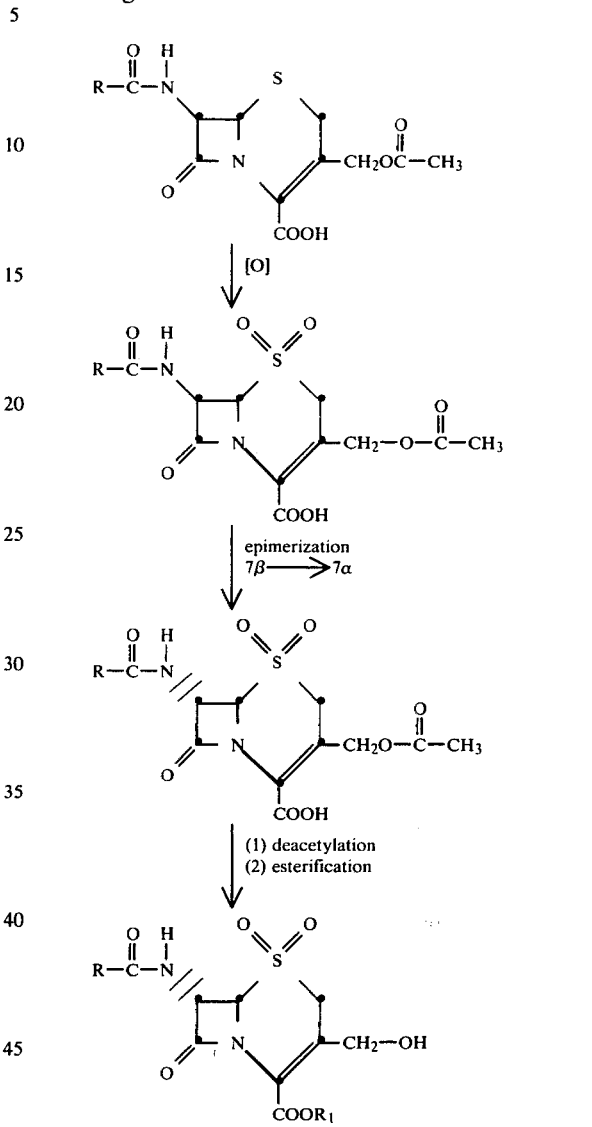

In the above formulas R and $R_1$ are as defined for formula 1.

The preparation of the cephalosporin sulfone is best carried out in an aqueous reaction medium maintained at a pH between about 5.0 and about 6.0 with an excess of potassium hydrogen persulfate. The oxidation proceeds well at temperatures of about 15° C. to about 45° C. The sulfone is recovered from the aqueous reaction medium by acidifying the mixture to form the free sulfone carboxylic acid and extraction of the latter with a suitable water immiscible solvent such as ethyl acetate.

The epimerization of the sulfone free acid is preferably carried out in an aqueous medium as follows. A slurry of the sulfone free acid in water is treated with an aqueous solution of sodium acetate containing at least one equimolar amount of sodium acetate. An aqueous solution of piperazine is then added dropwise until the pH of the solution is about 9.5 to 10. With the pH adjusted the epimerization mixture is stirred for about 5 to 15 minutes and the product recovered as follows. Ethyl acetate is added to the mixture which is then acidified to a pH of about 2.0 with concentrated hydrochloric acid. The epimeric sulfone free acid is then extracted with ethyl acetate.

The epimerization product, the 7α-acylaminocephalosporanic acid 1,1-dioxide, is then deacetylated with acetyl esterase to provide the epimeric 3-hydroxymethyl cephalosporin sulfone.

The deacetylation is preferably carried out with the esterase immobilized on a modified silica gel prepared as follows. Silica gel of 70–230 mesh and 62–200μ particle size (i.e. "Fractosil 200", E. Merck & Co.) is cleaned by first deaerating a slurry of the silica in aqueous 10% nitric acid, heating for 3 hours at about 80° C., and then rinsing with water. The cleaned silica gel is then slurried in 10 percent 3-aminopropyltriethoxysilane and the slurry deaerated under vacuum. The pH is adjusted to 3–4 with dilute hydrochloric acid and the slurry agitated periodically while heating at 80° C. for 3 hours. This modified silica is collected by filtration, washed with water, and dried for 16 hours at 105° C. The dried modified silica is slurried with aqueous 3 percent glutaraldehyde buffered by pH 7 phosphate (5–10 vol./wt. of silica). The slurry is periodically agitated during 3 hours and is then washed with water and pH 7 citrate buffer.

A neutral aqueous solution of the acetyl esterase is added to the aldehyde-silica and allowed to interact for about 20 hours. The silica-enzyme is then transferred to a glass column and washed with pH 7 citrate buffer.

The sulfone is dissolved in 0.2M aqueous sodium citrate and the pH of the solution adjusted to 7 with 1N sodium hydroxide. The solution is then passed over the silica-enzyme column. Ethyl acetate is added to the effluent and the mixture is chilled to 0° C. The pH of the cold mixture is adjusted to 2.5 with hydrochloric acid and the ethyl acetate layer is separated. The acidified aqueous phase is extracted further with ethyl acetate and all extracts are combined and washed with acidified brine and dried.

The 7α-acylamino-3-hydroxymethyl-3-cephem-4-carboxylic acid 1,1-dioxide is recovered from the ethyl acetate by evaporation. Alternatively, the washed and dried extract is concentrated in vacuo and the concentrate of the 3-hydroxymethyl sulfone is esterified. For example, the concentrate can be treated with diphenyldiazomethane to form diphenylmethyl 7α-acylamino-3-hydroxymethyl-3-cephem-4-carboxylate 1,1-dioxide.

Preferably, the esterification of the 3-hydroxymethyl sulfone acid is carried out by adding ethyl acetate containing a stoichiometric amount of diphenyldiazomethane to the effluent off the column. The 3-hydroxymethyl sulfone diphenylmethyl ester is recovered rather than first recovering the free acid and then esterifying. This preferred route of esterification diminishes the amount of lactone formed with the 3-hydroxymethyl group and the free carboxy group by intramolecular esterification.

The products obtained by the process of this invention are useful intermediates for the preparation of 1-oxa-β-lactam antibacterial compounds. For example, the 7α-acylamino-3-methyl-1-oxa-4-carboxylic acid in esterified form can be methoxylated in the 7-position with conversion of the 7-epi side chain to the natural or 7β-configuration. The methoxylation is carried out according to the procedure described by Narisada et al., U.S. Pat. No. 4,138,486. The methoxylation product is a 7β-acylamino-7α-methoxy substituted 1-oxa-β-lactam ester.

The 7-position side chains represented in the formula 1 by R—C(O)— are either the desired side chain of the ultimate antibacterial compound or are removable by known methods to provide the 7β-amino-7α-methoxy-1-oxa-β-lactam nucleus ester. The nucleus ester then can be reacylated with the appropriate carboxylic acid to provide the desired antibacterial compound. For example, the 7-position side chains of the compounds represented by the formula 1 wherein R is an alkoxy group or a substituted alkoxy group such as the benzyloxycarbonyl, diphenylmethoxycarbonyl, or t-butyloxycarbonyl are readily removed under mild acid conditions, e.g. with trifluoroacetic acid or formic acid. Likewise, the former two of the above-named groups can be removed reductively, e.g. by catalytic hydrogenolysis over 5% palladium on carbon.

The 1-oxa-β-lactam compounds obtained with the 3-methyl product as described hereinabove wherein R—C(O)— represents the α-protected aminoadipoyl side chain can be deacylated by the well-known N-deacylation procedure used in the preparation of 7-aminocephalosporanic acid and 7-aminodesacetoxycephalosporanic acid in the cephalosporain art. For example, the esterified and amino-protected 3-methyl-1-oxa compound, represented by the formula

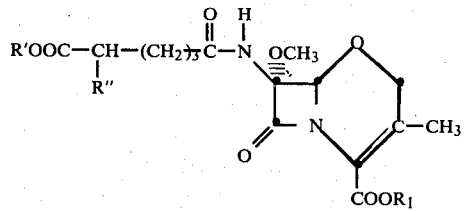

wherein $R_1$, R' and R'' have the same meanings as defined for formula 1, is reacted in a halogenated hydrocarbon solvent such as ethylene chloride or trichloroethane with phosphorus pentachloride in the presence of an organic base to provide the imino chloride derivative of the 7-position amide linkage. The imino chloride is then allowed to react with an alkyl alcohol or benzyl alcohol, preferably isobutanol, to provide the corresponding imino ether. The imino ether is decomposed with water or can decompose spontaneously to provide the 7β-amino-7α-methoxy-1-oxa-β-lactam ester. The latter can be reacylated by known procedures with the appropriate carboxylic acid to provide the desired product.

In the above-described N-deacylation of the protected aminoadipoyl group, the amino-protected groups R'' are preferred. These groups are prepared with cephalosporin C obtained by fermentation of Cephalosporium sp. These amino protected cephalosporin C derivatives, by virtue of their insolubility, are useful in obtaining greater amounts of cephalosporin C from fermentation broths and column chromatography resin eluates. Such derivatives are converted, via the reaction sequence described hereinabove, to the corresponding 1-oxa-β-lactam compounds. Upon N-deacylation the amino-protected α-aminoadipoyl group is cleaved from the 1-oxa-β-lactam to provide the amino-1-oxa-β-lactam nucleus.

The compounds represented by the formula 1 wherein R is the 4-carboxybutyl group $HOOC(CH_2)_3$, or the 4-formylbutyl group OCH(CH₂)₃, are obtained from cephalosporin C and desacetylcephalosporin C. These desamino cephalosporin C derivatives are obtained as described by Suzuki et al., U.S. Pat. No. 4,079,180, Mar. 14, 1978. These desamino side chains of the 1-oxa-β-lactams are deacylated to the 7-amino nucleus compound by the N-deacylation process described above for the 1-oxa product having the α-aminoadipoyl side chain. An especially valuable process for this N-deacylation is described by Hatfield et al., U.S. Pat. No. 4,211,702, July 8, 1980.

The 3-exomethylene-1-oxa-β-lactam compounds provided by this invention are also useful as intermediates in the preparation of 3-alkoxy and 3-halo substituted 1-oxa antibiotic compounds. For example, the compound represented by the formula

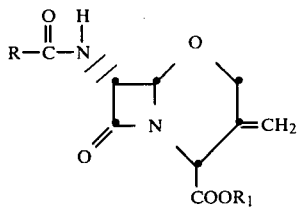

wherein R and R₁ have the same meanings as defined for formula 1, is methoxylated to the 7β-acylamino-7α-methoxy-3-exomethylene ester and the latter is reacted with ozone to form the 3-hydroxy ester represented by the formula

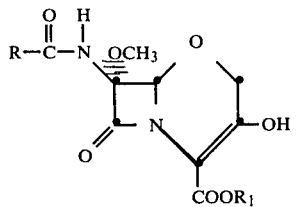

The 3-hydroxy-1-oxa-ester can be reacted with diazomethane to form the corresponding 3-methoxy compound or alternatively with phosphorus trichloride in dimethylformamide to form the 3-chloro ester. Following these reactions at the 3-position the desired 7-position side chain can be attached by either the removal of formula 1 side chain and reacylation with the appropriate carboxylic acid or by deblocking any protecting groups to form the desired side chain with free amino, hydroxy or carboxy substituents.

In a further aspect this invention provides the epi compounds represented by the following formula

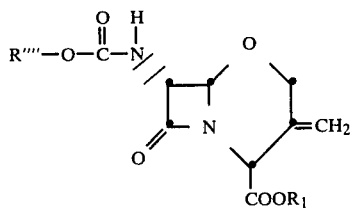

wherein R'''' and R₁ have the same meanings as defined for formula 1. Preferred compounds are represented when R'''' is benzyl, substituted benzyl, or diphenylmethyl. Examples of preferred compounds are represented when R'''' is benzyl, methyl substituted benzyl, e.g. 4-methylbenzyl, and R₁ is diphenylmethyl.

This invention is further illustrated by the following Examples.

EXAMPLE 1

Approximately 990 mg. of 1-(2-hydroxymethyl-3-diphenylmethoxycarbonylpropene-3-yl)-3α-benzyloxycarbamidoazetidin-2-one-4-sulfinic acid (obtained by the electrolysis of 1.15 g. of diphenylmethyl 7α-benzyloxycarbamido-3-hydroxymethyl-3-cephem-4-carboxylate 1,1-dioxide) was dissolved in liquid sulfur dioxide and 800 mg. of lead tetraacetate and 15 mg. of copper sulfate were added to the solution with stirring. The reaction mixture was stirred for about 20 minutes and was quenched by adding ethyl acetate and water. The organic layer was separated from the aqueous phase and washed with three 25 ml. portions of pH 7.0 buffer: brine, 50:50, v:v. The organic layer was dried over magnesium sulfate, filtered and evaporated to dryness. There were obtained about 500 mg. of the product as a white foam. A portion of the product (200 mg.) was chromatographed on silica gel using ethyl acetate: toluene, 3:2, v:v for development. The lead zone, which was shown by both iodine and UV development, was recovered to provide 60 mg. of the crude product. The 60 mg. of product were purified on a Water's Associates C₁₈ reverse phase HPLC column using 70% acetonitrile-water as eluent.

The HPLC showed two peaks, each of which were collected and yielded respectively 11.4 mg. of the 3-exomethylene-1-oxa-β-lactam ester represented by the formula

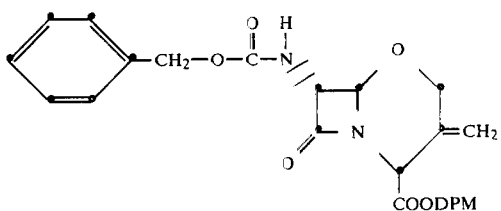

IR: β-lactam carbonyl absorption at 1780 cm⁻¹.
Ester carbonyl absorption at 1760 cm⁻¹.
Field Desorption Mass Spec.: 498; and 12.0 mg. of the isomeric 3-methyl-3-cephem represented by the formula

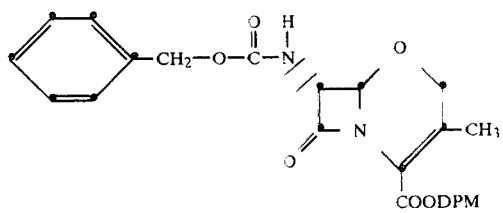

Field Desorption Mass Spec.: 498.

EXAMPLE 2

Diphenylmethyl 7α-benzyloxycarbamido-3-hydroxymethyl-3-cephem-4-carboxylate 1,1-dioxide (562 mg.) in acetonitrile:acetic acid, 34:2,v:v, was reduced at a temperature of about 0° C. at the mercury cathode of an electrolytic cell at a reduction potential of −1.450 v.

(vs. standard calomel electrode) for about 3 hours. The reduction mixture was kept cold and 100 ml. of cold ethyl acetate were added. The cold organic layer was separated and was washed three times with 80 ml. portions of pH 7.0 phosphate buffer:brine, 1:1, v:v. After washing, the organic layer containing the azetidin-2-one-4-sulfinic acid was dried over magnesium sulfate and filtered.

The ethyl acetate solution of the sulfinic acid was cooled in a dry ice-acetone bath and 400 mg. of lead tetraacetate were added. The reaction mixture was stirred in the cold for about 2 hours during which time the temperature was allowed to rise to about $-5°$ C. to about $0°$ C. An additional 200 mg. of lead tetraacetate were added and stirring was continued for about 45 minutes. The reaction mixture was filtered to remove lead tetraacetate and the filtrate was washed three times with 75 ml. portions of 0.3M pH 7.0 phosphate buffer:brine, and then dried over magnesium sulfate. The dried solution was evaporated to dryness and the residue of reaction products was dissolved in chloroform. The chloroform solution was concentrated to initiate crystallization of some side product (ca. 20 mg.) which appeared to be the lactone of the 1,1-dioxide starting material used in the electrolytic reduction.

The above filtrate was chromatographed on preparative thin layer silica gel plates using ethyl acetate:toluene, 3:2 v:v, for development. Five zones were developed and each were extracted from the silica gel. Zone 2 afforded 21.9 mg. and was chromatographed via reverse phase HPLC $C_{18}$ silica gel. The largest peak in the HPLC was collected and evaporated to yield the 3-methyl-1-oxa compound represented by the following formula

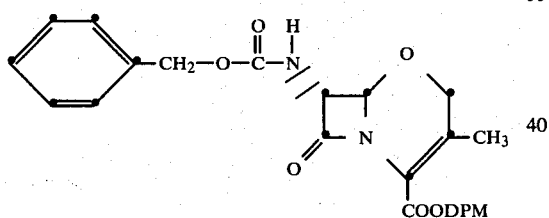

Mass Spec.: 498.

NMR (360 Hz., DMSOd$_6$): signals at 1.93 (s, 3H, 3—CH$_3$), 4.41 (s, 2H, C$_2$—H), 4.49 (d, J=8–9 Hz, 1H, C$_7$—H), 5.06 (s, 1H, C$_6$—H), 5.10 (s, 2H, benzyl CH$_2$), 6.87 (s, 1H, benzhydryl H), 8.39 (d, J=8–9 Hz, 1H, amide H), and 7.2–7.6 (15 aromatic H), ppm.

The two smaller peaks in the zone 2 HPLC contained the corresponding 3-exomethylene isomer.

EXAMPLE 3

A solution of 1 g. of diphenylmethyl 7α-phenoxyacetamido-3-hydroxymethyl-3-cephem-4-carboxylate 1,1-dioxide in 36 ml. of methyl alcohol was placed in an electrolytic cell (comprising a mercury ring cathode, a platinum wire ring anode, a standard calomel electrode, 0.1M sodium perchlorate catholyte, and 1M pH 2 phosphate anolyte) and reduced at a temperature of about $0°$ C. at $-1.45$ v. After the electrolysis was complete the cold electrolyte was transferred to a 250 ml. separatory funnel and 80 ml. of cold ethyl acetate were added. The cold mixture was washed with 50 ml. of 1:1, brine: 0.3M phosphate pH 7 buffer. The ethyl acetate was separated, a fresh 80 ml. of cold ethyl acetate were added and extracted again. The ethyl acetate extracts were combined and washed three times with the brine-phosphate buffer and were then dried over magnesium sulfate. The dried extract was evaporated to dryness to provide 765 mg. of the electrolysis product, crude 1-(2-hydroxymethyl-3-diphenylmethoxycarbonyl-propene-3-yl)-3α-phenoxyacetamidoazetidin-2-one-4-sulfinic acid.

The azetidin-2-one-4-sulfonic acid was added to a 3-necked flask equipped with a Dewar condenser (dry ice-acetone), a stopper and a gas inlet tube. Copper sulfate (15 mg.) was added to the flask and sulfur dioxide was then added until about 12 ml. of liquid SO$_2$ was formed. When the solids had dissolved 600 mg. of lead tetraacetate were added. The reaction was allowed to proceed for 10 minutes and was then added to a separatory funnel containing 80 ml. of ethyl acetate and 80 ml. of 1:1, v:v, brine:pH 7.0 phosphate buffer mixture. The ethyl acetate layer was separated and washed three times with the brine-phosphate mixture and then dried over magnesium sulfate. The ethyl acetate solution was filtered from the drying agent and evaporated to dryness to yield 443 mg. of crude product.

The crude product mixture was chromatographed on reverse phase $C_{18}$ silica HPLC using 50% acetonitrile-H$_2$O to provide the 7α-phenoxyacetamido-3-methyl-Δ3-1-oxa-β-lactam-4-carboxylic acid diphenylmethyl ester represented by the formula

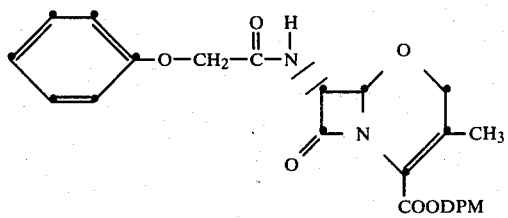

Field Desorption Mass Spec.: mass ion 498.

NMR (90 Hz, DMSOd$_6$): signals at 1.90 (s, 3H, C$_3$ methyl), 4.40 (s, 2H, C$_2$—H), 4.59 (s, 2H, phenoxyacetyl CH$_2$); 4.74 (d of d, $J^{4H}=1.5$ Hz and $J^{NH}=9.4$ Hz, 1H, C$_7$—H), 5.11 (d, $J^{3H}=1.5$ Hz, 1H, C$_6$—H), 6.90 (s, 1H, ester methine H), 7–7.8 (m, aromatic H), and 9.11 (d, $J^{3H}=9.4$ Hz, 1H, amide H) ppm.

EXAMPLE 4

A solution of 1-(2-hydroxymethyl-3-diphenylmethoxycarbonylprop-1-ene-3-yl)-3α-benzyloxycarbamidoazetidin-2-one-4-sulfonic acid, obtained by the electrolytic reduction of 1.051 g. of diphenylmethyl 7α-benzyloxycarbamido-3-hydroxymethyl-3-cephem-4-carboxylate, 1,1-dioxide, in about 25 ml. ethyl acetate was cooled in an ethanol-ice bath and approximately 50 ml. of boron trifluoride etherate and 800 mg. of lead tetraacetate were added. The reaction mixture was stirred in the cold for about 1.5 hours. The reaction was monitored by HPLC which showed the reaction was completed in about 20 minutes. The reaction mixture was filtered and the filtrate washed with pH 7.0 phosphate buffer mixed with brine and then was evaporated to dryness. There were obtained 380 mg. of the product mixture as a white foam. Multiple reverse phase $C_{18}$ silica HPLC chromatograms were run on the mixture to provide a substantially pure sample of the 3-exomethylene-1-oxa compound represented by the formula

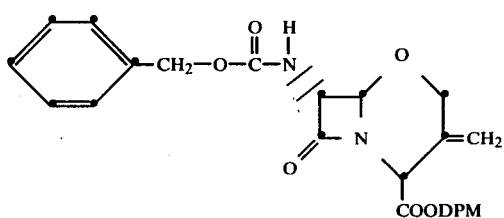

Field Desorption Mass Spec.: Mass ion=498.

NMR (360 Hz, DMSOd$_6$): signals at 4.28 (ABq, 2H, C$_2$—H), 4.45 (d, J=8.5 Hz, 1H, C$_7$—H), 5.11 (s, 2H, benzyl CH$_2$), 5.23 (s, 1H, C$_4$—H), 5.39 and 5.43 (s, s, 2H, 3-exomethylene H), 5.46 (s, 1H, C$_6$—H), 6.85 (s, 1H, ester methine H), 7.25–7.55 (m, aromatic H), and 8.33 (d, J=8.5 Hz, 1H, amide H) ppm.

IR: 1775 cm$^{-1}$, β-lactam carbonyl, and 1730 cm$^{-1}$ ester carbonyl.

Another peak in the HPLC contained a mixture of the 3-methyl isomer and the 4α- and 4β-forms of the above 3-exomethylene isomer. This mixture in the infrared showed absorption maxima at 1775 cm$^{-1}$ and 1730 cm$^{-1}$ for the β-lactam carbonyl and ester carbonyl functions, respectively.

I claim:

1. A process for preparing a compound of the formula

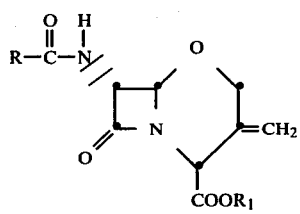

and the isomer thereof of the formula

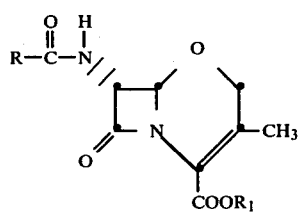

which comprises mixing at a temperature between about −25° C. and about 0° C. in an inert organic solvent between about 1 mole and about 2.5 moles of lead tetraacetate per mole of an azetidin-2-one sulfinic acid of the formula

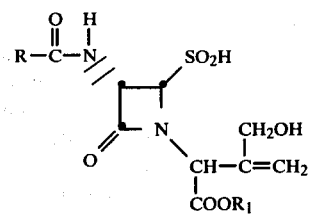

where in the above formulas R is hydrogen, C$_1$–C$_4$ alkyl, or an α-(protected amino)-4-carboxybutyl group of the formula

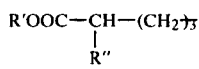

wherein
R′ is a carboxy-protecting group and
R″ is a protected amino group; or R is a group represented by the formula

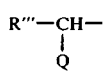

wherein R‴ is thienyl, furyl, tetrazolyl, 1,4-cyclohexadienyl, cyclohexenyl, phenyl, or a substituted phenyl group of the formula

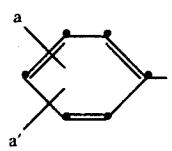

wherein
a and a′ independently are hydrogen, C$_1$–C$_4$ alkyl, fluoro, chloro, protected amino, protected aminomethyl, protected carboxy, protected carboxymethyl, carbamoyl, C$_1$–C$_4$ alkoxy, or protected hydroxy;
Q is hydrogen, protected amino, protected carboxy, or protected hydroxy;
or R is an aryloxymethyl group of the formula

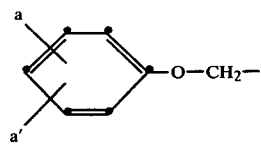

wherein
a and a′ have the same meanings as defined above;
or R is an alkoxy or substituted alkoxy group represented by the formula

wherein
R″″ is C$_1$–C$_5$ alkyl, C$_3$–C$_6$ cycloalkyl, benzyl, benzyl substituted by C$_1$–C$_4$ alkyl, C$_1$–C$_4$ alkoxy, or chloro;
and R$_1$ is a carboxy-protecting group.

2. The process of claim 1 wherein R is an alkoxy group or substituted alkoxy group.

3. The process of claim 2 wherein R is benzyloxy.

4. The process of claim 2 wherein the azetidin-2-one is mixed with lead tetraacetate in the presence of a carbonium ion stabilizing compound.

5. The process of claim 4 wherein R is benzyloxy and the carbonium ion stabilizing compound is sulfur dioxide.

6. The process of claim 1 wherein R is other than an alkoxy or substituted alkoxy group and the azetidin-2-one sulfinic acid is mixed with lead tetraacetate in the presence of a carbonium ion stabilizing compound.

7. The process of claim 6 wherein R is phenoxymethyl.

8. The process of claim 7 wherein the carbonium ion stabilizing compound is sulfur dioxide.

9. The process of claim 8 carried out in the presence of copper II ion.

* * * * *